United States Patent [19]

Gibson

[11] 4,340,671

[45] Jul. 20, 1982

[54] *E. COLI* SENSITIVITY BROTH

[75] Inventor: Sandra F. Gibson, St. Louis, Mo.

[73] Assignee: McDonnell Douglas Corporation, St. Louis, Mo.

[21] Appl. No.: 153,194

[22] Filed: May 27, 1980

Related U.S. Application Data

[63] Continuation-in-part of Ser. No. 828,944, Aug. 29, 1977, abandoned.

[51] Int. Cl.³ .............................................. C12Q 1/18
[52] U.S. Cl. ........................................ 435/32; 435/33; 435/34; 435/37; 435/38; 435/253
[58] Field of Search ...................... 435/32, 33, 34, 38, 435/253, 37

[56] References Cited

U.S. PATENT DOCUMENTS

| | | | |
|---|---|---|---|
| 3,043,751 | 7/1962 | Goldman | 435/32 |
| 3,063,916 | 11/1962 | Kosikowski | 435/32 |
| 3,107,204 | 10/1963 | Brown et al. | 435/33 |
| 3,216,907 | 11/1965 | Goldman | 435/32 X |
| 4,000,041 | 12/1976 | Lanham et al. | 435/37 |

*Primary Examiner*—Robert J. Warden
*Attorney, Agent, or Firm*—Gravely, Lieder & Woodruff

[57] ABSTRACT

A medium for determining *Escherichia coli* sensitivity to a pre-selected antimicrobial agent. The medium contains nutrient sources, inhibitors to inhibit growth of gram-positive and of other gram-negative micro-organisms, and an indicator which will show metabolic activity or lack thereof by *E. coli* in the medium, and a specific antimicrobial agent whose effectiveness against *E. coli* is being tested. If a given agent is effective against *E. coli* when *E. coli* is added to the medium containing that agent, the medium will remain clear. If the specific agent is ineffective against *E. coli* the color of the medium containing *E. coli* and that agent will change to blue as the *E. coli* metabolizes in the medium and produces acid.

15 Claims, No Drawings

E. COLI SENSITIVITY BROTH

REFERENCE TO OTHER APPLICATIONS

This application is a continuation-in-part of Ser. No. 828,944 filed Aug. 29, 1977 now abandoned and contains subject matter in common with U.S. Pat. Nos. 3,957,583 dated May 18, 1976, entitled *APPARATUS AND PROCESS FOR DETERMINING THE SUSCEPTIBILITY OF MICROORGANISMS TO ANTIBIOTICS;* and 4,000,041 dated Dec. 28, 1976, entitled *E. COLI IDENTIFICATION BROTH;* and copending U.S. application Ser. Nos. 682,253 filed May 13, 1976, entitled *BROTH FOR DETECTING E. COLI IN WATER SAMPLES;* (now U.S. Pat. No. 4,072,575) and Ser. No. 682,651 filed May 3, 1976, entitled *E. COLI DETECTION BROTH FOR CLINICAL USE WITH AUTOMATED MICROBIAL ANALYZER* (now U.S. Pat. No. 4,072,572).

BACKGROUND OF THE INVENTION

Gibson et al, U.S. Pat. No. 3,957,583 discloses a process and apparatus for conducting antibiotic susceptibility tests in a relatively short time. In U.S. Pat. No. 3,957,583, the clinical specimen is examined directly without isolating the suspected microorganisms. The basic process of U.S. Pat. No. 3,957,583 involves introducing a specimen into blends of a selective culture medium and known antimicrobial agents. If the specimen contains a microorganism which is favored by the culture medium of a blend, and the microorganism is not susceptible to the agent, the optical characteristics of the blend will change.

When the concentration of organisms reaches $10^5$ in a well, the mechanism disclosed in U.S. Pat. No. 3,957,583 will indicate a positive reading and then a 100 to 1 dilution is made when the organism is inoculated into the media contained in the wells of this invention. The wells are covered with a tape which allows a limited and controlled amount of oxygen to flow into the microenvironment of the well.

The major problem encountered with conventional microbial sensitivity tests is the length of time that passes from obtaining a clinical specimen from the patient to selection of a suitable antimicrobial agent that can be expected to control any microorganisms detected. U.S. Pat. No. 4,000,041 discloses a medium for detecting *E. Coli* microorganisms. However, that patent falls short of disclosing how to determine the susceptibility of *E. Coli* microorganisms to a given set of antibiotics. Accordingly, it is an object of the present invention to provide a medium which, when used with the apparatus described in U.S. Pat. No. 3,957,583, will allow a clinician to determine within a relatively short period of time (from about 8 to about 12 hours) which of a series of antimicrobial agents will be effective in suppressing the activity of infectious microorganisms.

One other problem is present in the present application that is not a problem in conventional antibiotic sensitivity compositions. Namely, it is critical that the composition of the present application be adhered to strictly because of the microenvironment in which it is placed. The apparatus of U.S. Pat. No. 3,957,583 uses wells which accept only about 17 microns of dried medium and there is less than one microliter of antibiotic in the well. With the amounts of ingredients at this micro level, the intermolecular or electrostatic action between the minute quantities of ingredients in each well may affect the ability of the ingredients to react on the same level and in exactly the same manner as when using larger amounts. Antibiotics are particularly susceptible to this problem. The close confines of the small well also restrict the activity of the organism and the reactivity of chemicals and antibiotics are not predictable in this environment.

Another matter which is significant in the apparatus of U.S. Pat. No. 3,957,583 is that the flow of oxygen to the ingredients in the well must be controlled. In other words, the wells in which the medium is placed have a controlled oxygen ($O_2$) environment and for this purpose, certain chemicals are included in the various media. Also as mentioned, the tape covering each well has a controlled and limited oxygen permeability.

It is also important to prevent release of chloride ions in the rehydrated medium to prevent the medium from becoming acid and giving a false positive as the metabolism of *E. Coli* itself produces an acidic change in the medium which change is shown by the change in color of the indicator. All of these problems are so much more significant when one is using a microsystem and make the standard full scale methodology inapplicable and not transferable to the present application.

The broth of the present invention will allow the clinician to test several antibiotics simultaneously to determine *E. Coli* sensitivity. The results obtained allow the clinician to select a primary antibiotic and also allow him to select a group of backup antibiotics, should the primary antibiotic fail to treat the patient's condition.

SUMMARY OF THE INVENTION

This invention involves a medium for determining sensitivity of *E. Coli* organisms to pre-selected antimicrobial agents in a microenvironment. The medium contains carbon and nitrogen nutrient sources, inhibitors to inhibit the growth of gram-positive organisms and other gram-negative organisms which may give false positives for *E. Coli,* and a color indicator which shows metabolic activity in the medium. The basic medium also includes a pre-selected agent whose effectiveness against *E. Coli* is measured by the aforesaid color indicator which indicates metabolism of *E. Coli.*

DETAILED DESCRIPTION

The culture medium of the present invention contains from about 5 to about 15 g/l of a carbon source which is assimilated by *E. Coli;* about 10 to about 30 ml of an indicator which indicates the positive growth and metabolism of *E. Coli* organism by turning color in response to production of an acid by metabolic activity of the *E. Coli* organism in the medium; about 1.5 to about 4.5 g/l surfactant or other inhibitor of gram-positive organisms; about 2.5 to about 7.5 g/l nitrogen source; about 1.5 g/l to about 4.5 g/l coumaric acid to inhibit the growth of other coliform-like gram-negative organisms which, by current methods, often give positive results in tests for *E. Coli;* about 0.25 g/l to about 0.75 g/l of a mineral and vitamin source; and about 2 µg/ml to about 40 µg/ml of an antibiotic; this antibiotic is, in effect, being tested for its effectiveness in preventing metabolism of *E. Coli.*

The major carbon source is lactose. The purpose of the lactose is to provide a source of energy for metabolism and growth of the coliform organisms. These organisms, including *E. Coli,* ferment lactose and produce acids, so that the use of lactose is important to this medium. Utilization of lactose by *E. Coli* is known in the art. Another source of carbon used is L-arabinose which is used in the detection medium because it is able to be fermented by the less than 10% of the strains of *E. Coli* that do not readily ferment lactose. Thus, this medium, which uses a combination of sugars, will be responsive to all strains of *E. Coli*.

Suitable cources of nitrogen are proteins or peptones, such as Gelysate, Trypticase, Phytone, and Polypeptone. These materials provide a source of nitrogen required for complete metabolic activity of the organism.

Suitable surfactants are Bile Salts Mixture from BBL of Bile Salts No. 3 from Exoid, and similar products made by other manufacturers. The purpose of the bile salts is to inhibit growth of gram-positive organisms. Additional compounds which may be added to inhibit growth of gram-positive bacteria are desoxycholic acid (0.1–1.0%); cholic acid (0.1–1.0%); taurodeoxycholic acid (0.05–0.25%); lithocholic acid (0.005–0.045%); taurocholic acid (0.1–0.3%); Brilliant Green (0.001–0.008%); crystal violet (0.0001–0.00005%); and Tergitol 7 (0.005–0.1%). Gram-positive organisms are, as a class, susceptible to surfactant-like materials.

A suitable mineral and vitamin source is yeast extract.

A suitable biological pH indicator is reduced or decolorized aniline blue. The aniline blue is described in detail in copending application Ser. No. 682,652 of Aldridge and Meyer, filed May 3, 1976, entitled *SENSITIVE PH INDICATOR*, now U.S. Pat. No. 4,062,876. The aniline blue measures change of pH toward acid and turns from clear to a blue color as the pH moves toward acid.

The chemical inhibitor courmaric acid acts to selectively inhibit the metabolic activity of *Klebsiella* and *Enterobacter* species without appreciably affecting the metabolic activity of *E. Coli*.

Both meta-coumaric acid and ortho-coumaric acid can be used in this invention. However, para-coumaric acid is much more effective than either the meta or ortho species.

The specific ingredients and the amounts thereof are critical and essential to the proper functioning of the medium in the microenvironment of the well with the diluted specimen of *E. Coli* present. These ranges of ingredients differentiate these media from the media disclosed in U.S. Pat. No. 4,000,041. Also the present media contains L-arabinose and yeast extract which are not shown in U.S. Pat. No. 4,000,041 as well as the added antibiotic.

As previously mentioned, the microenvironment of this invention and the higher concentrations of ingredients and the limited oxygen access all seem to make the composition and the action of any organism or ingredient unpredictable.

In addition to the foregoing, an antibiotic is added to the medium to determine the sensitivity of *E. Coli* to the particular antibiotic being tested. The following antibiotics may be used in this invention within the ranges specified:

Cephalothin (Sodium)—about 7 µg to about 21 µg/ml
Nalidixic Acid—about 10 µg to about 30 µg/ml
Ampicillin Trihydrate—about 15 µg to about 30 µg/ml
Sodium Colistimethate—about 2 µg to about 7 µg/ml
Nitrofurantoin—about 20 µg to about 40 µg/ml
Tetracycline HCl—about 7 µg to about 15 µg/ml
Gentamicin Sulfate—about 2.5 µg to about 7 µg/ml
Kanamycin Sulfate—about 6 µg to about 15 µg/ml
Trimethoprim-Sulfamethoxazole (1:20)—about 7 µg to about 15 µg/ml
Sodium Carbencillin—about 20 µg to about 40 µg/ml
Chloramphenicol—about 15 µg to about 25 µg/ml The foregoing amounts are based on activity.

EXAMPLE I

To prepare a 2X medium in an amount of 100 ml, *E. Coli* sensitivity broth is prepared by adding 9.0 gm of p-coumaric acid to 45 ml of 1 N NaOH. The mixture is heated until the p-coumaric acid dissolves. The pH is adjusted to 7.0 using 1 N HCl. Sufficient distilled water is added to the mixture until a volume of 1500 ml is attained. The following nutrients are added to the mixture after the dissolution of the coumaric acid:

Gelysate—15.0 gm
Lactose—15.0 gm
L-Arabinose—15.0 gm
Biles Salts Mixture—9.0 gm
Yeast Extract—1.5 gm The order of addition is critical in order to avoid hydrolyzing the lactose. After all of the foregoing ingredients are dissolved, the pH is adjusted to 7.0.

60 ml of reduced aniline blue reagent prepared according to the disclosure of Ser. No. 682,652 are added to the mixture. The pH should then be adjusted, if necessary, to 7.5 and the medium is filter sterilized. Base may be added if necessary, but acid should not be added.

Twelve 100 ml aliquots are removed from the mixture. Each aliquot is placed in a pre-labeled anti-biotic beaker.

The following antibiotics in the respective amounts are used per 100 ml of the medium:

Cephalothin (Sodium)—2,800 µg
Nalidixic Acid—4,000 µg
Ampicillin Trihydrate—4,200 µg
Sodium Colistimethate—1,000 µg
Nitrofurantoin—6,000 µg
Tetracycline HCl—2,000 µg
Gentamicin Sulfate—600 µg
Kanamycin Sulfate—1,600 µg
Trimethoprim-Sulfamethoxazole (1:20)—2,000 µg
Sodium Carbenicillin—6,000 µg
Chloramphenicol—4,000 µg The foregoing amounts are based on activity.

The media are freeze dried and added to the microenvironment (a cell closed with a tape of controlled limited oxygen permeability as in U.S. Pat. No. 3,957,583). An amount of dried ingredients of less than about 20 microns, preferably about 17 microns, is added to each microenvironmental space.

In use a polymicrobial specimen known to contain at least $10^5$ *E. Coli* organisms is diluted 100 to 1 with distilled water and injected into the microenvironment in an amount of less than about 1.5 microliters, preferably about 1.1 microliters.

The microenvironment then is observed for signs that the preselected antibiotic is effective against *E. Coli*.

What is claimed is:

1. In a microenvironment having accommodation for less than about 20 microns of dried medium and less than about 1 microliter of antibiotic and having a controlled limited oxygen ($O_2$) accessibility, the improvement of a selective broth medium for determining *Escherichia Coli* sensitivity from a polymicrobic specimen to an antibiotic consisting essentially of:

(a) from about 1.5 to about 4.5 g/l coumaric acid to inhibit the growth of gram negative organisms other than *E. Coli* which normally give positive results in tests for *E. Coli*, (b) from about 5 to about 15 g/l lactose and L-arabinose carbon source, (c) from about 2.5 to about 7.5 g/l nitrogen source, (d) from about 1.5 to about 4.5 g/l gram-positive organism inhibitor, (e) from about 0.25 to about 0.75 g/l mineral and vitamin source, (f) from about 10 to about 30 ml reduced aniline blue indicator to visually show the metabolism of *E. Coli* organism, (g) said carbon, nitrogen, mineral and vitamin sources containing a material metabolized by *E. Coli* to produce acid to trigger the indicator so that it turns blue, and (h) a preselected antibiotic at a pH of about 7.5.

2. The medium of claim 1 wherein the antibiotic is Cephalothin (Sodium), said antibiotic being present at a concentration of about 7 $\mu$g to about 21 $\mu$g/ml, based on activity.

3. The medium of claim 1 wherein the antibiotic is Nalidixic Acid, said antibiotic being present at a concentration of about 10 $\mu$g to about 30 $\mu$g/ml, based on activity.

4. The medium of claim 1 wherein the antibiotic is Ampicillin Trihydrate, said antibiotic being present at a concentration of about 15 $\mu$g to about 30 $\mu$g/ml, based on activity.

5. The medium of claim 1 wherein the antibiotic is Sodium Colistimethate, said antibiotic being present at a concentration of about 2 $\mu$g to about 7 $\mu$g/ml, based on activity.

6. The medium of claim 1 wherein the antibiotic is Nitrofurantoin, said antibiotic being present at a concentration of about 20 $\mu$g to about 40 $\mu$g/ml, based on activity.

7. The medium of claim 1 wherein the antibiotic is Tetracycline HCl, said antibiotic being present at a concentration of about 7 $\mu$g to about 15 $\mu$g/ml, based on activity.

8. The medium of claim 1 wherein the antibiotic is Gentamicin Sulfate, said antibiotic being present at a concentration of about 2.5 $\mu$g to about 7 $\mu$g/ml, based on activity.

9. The medium of claim 1 wherein the antibiotic is Kanamycin Sulfate, said antibiotic being present at a concentration of about 6 $\mu$g to about 15 $\mu$g/ml, based on activity.

10. The medium of claim 1 wherein the antibiotic is Trimethoprim-Sulfamethoxazole (1:20), said antibiotic being present at a concentration of about 7 $\mu$g to about 15 $\mu$g/ml, based on activity.

11. The medium of claim 1 wherein the antibiotic is Sodium Carbenicillin, said antibiotic being present at a concentration of about 20 $\mu$g to about 40 $\mu$g/ml, based on activity.

12. The medium of claim 1 wherein the antibiotic is Chloramphenicol, said antibiotic being present at a concentration of about 15 $\mu$g to about 25 $\mu$g/ml, based on activity.

13. A method of determining *Escherichia Coli* sensitivity to a preselected antibiotic comprising:

(a) preparing a selective broth medium having a pH of about 7.5 consisting essentially of:

(1) from about 1.5 to about 4.5 g/l coumaric acid to inhibit the growth of gram negative organisms other than *E. Coli* which normally give positive results in tests for *E. Coli*, (2) from about 5 to about 15 g/l lactose and L-arabinose carbon source, (3) from about 2.5 to about 7.5 g/l nitrogen source, (4) from about 1.5 to about 4.5 g/l gram-positive organism inhibitor, (5) from about 0.25 to about 0.75 g/l mineral and vitamin source, (6) from about 10 to about 30 ml reduced aniline blue indicator to visually show the metabolism of *E. Coli* organism, (7) said carbon, nitrogen, mineral and vitamin sources containing a material metabolized by *E. Coli* to produce acid to trigger the indicator so that it turns blue, and (8) a preselected antibiotic, (b) freeze drying the said medium, (c) loading the medium into a microenvironment having accomodation for less than about 20 microns of dried medium and less than about 1 microliter of antibiotic and having controlled limited oxygen accessibility, (d) inoculating the medium in the said microenvironment with a polymicrobic specimen known to contain at least $10^5$ *E. Coli* organism, and (e) observing the medium for a change in the light transmitting properties to indicate the effectiveness of the preselected antibiotic to *E. Coli*.

14. The method of claim 13 wherein the coumaric acid is para-coumaric acid.

15. The method of claim 13 wherein the preselected antibiotic is selected from the group consisting of Cephalothin (Sodium), Nalidixic Acid, Ampicillin, Sodium Colistimethate, Nitrofurantoin, Tetracycline, Gentamicin Sulfate, Kanamycin, Trimethoprim-sulfamethoxazole, Carbenicillin, and Chloramphenicol.

* * * * *